(12) United States Patent
Bakhle et al.

(10) Patent No.: US 10,278,963 B2
(45) Date of Patent: May 7, 2019

(54) PHARMACEUTICAL COMPOSITIONS OF DONEPEZIL HAVING SPECIFIC IN VITRO DISSOLUTION PROFILE OR PHARMACOKINETICS PARAMETERS

(71) Applicant: Lupin Limited, Mumbai, Maharashtra (IN)

(72) Inventors: Dhananjay Sadashiv Bakhle, Maharashtra (IN); Chirag Anilkumar Shah, Maharashtra (IN); Snehal Ameet Gadve, Maharashtra (IN); Neha Sharma, Maharashtra (IN); Sajeev Chandran, Maharashtra (IN); Ashish Ashokrao Deshmukh, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 14/771,225

(22) PCT Filed: Feb. 27, 2014

(86) PCT No.: PCT/IB2014/059298
§ 371 (c)(1),
(2) Date: Aug. 28, 2015

(87) PCT Pub. No.: WO2014/132215
PCT Pub. Date: Sep. 4, 2014

(65) Prior Publication Data
US 2016/0008335 A1    Jan. 14, 2016

(30) Foreign Application Priority Data
Feb. 28, 2013   (IN) .............. 990/KOL/2012

(51) Int. Cl.
| | |
|---|---|
| *A61K 9/16* | (2006.01) |
| *A61K 31/445* | (2006.01) |
| *A61K 9/00* | (2006.01) |
| *A61K 9/20* | (2006.01) |
| *A61K 9/28* | (2006.01) |
| *A61K 9/50* | (2006.01) |

(52) U.S. Cl.
CPC .......... *A61K 31/445* (2013.01); *A61K 9/0004* (2013.01); *A61K 9/167* (2013.01); *A61K 9/2018* (2013.01); *A61K 9/2054* (2013.01); *A61K 9/2086* (2013.01); *A61K 9/2846* (2013.01); *A61K 9/2866* (2013.01); *A61K 9/5026* (2013.01); *A61K 9/5078* (2013.01)

(58) Field of Classification Search
None
See application file for complete search history.

(56) References Cited

U.S. PATENT DOCUMENTS

| | | |
|---|---|---|
| 2005/0232990 A1 | 10/2005 | Boehm et al. |
| 2006/0159753 A1 | 7/2006 | Ueki et al. |
| 2006/0252788 A1 | 11/2006 | Went et al. |
| 2006/0280789 A1 | 12/2006 | Ueki et al. |
| 2007/0129402 A1 | 6/2007 | Ueki et al. |
| 2008/0213368 A1 | 9/2008 | Ueki et al. |
| 2009/0208579 A1* | 8/2009 | Ueki ............... A61K 9/2018 424/487 |
| 2010/0152164 A1 | 6/2010 | Ueki et al. |
| 2011/0045074 A1 | 2/2011 | Ueki et al. |
| 2011/0218216 A1 | 9/2011 | Vivek et al. |
| 2011/0237623 A1 | 9/2011 | Penhasi et al. |

FOREIGN PATENT DOCUMENTS

| | | |
|---|---|---|
| WO | WO 2011/069076 A2 | 6/2011 |
| WO | WO-2012016708 A1 * | 2/2012 ........... A61K 9/2009 |
| WO | WO 2012/035409 A1 | 3/2012 |

OTHER PUBLICATIONS

International Search Report and Written Opinion of the International Searching Authority for International Patent Application No. PCT/IB2014/059302 (dated Jun. 16, 2014).
International Search Report and Written Opinion of the International Searching Authority for International Patent Application No. PCT/IB2014/059298 (dated Jun. 16, 2014).
Martin Farlow et al.: "Safety and Tolerability of Donepezil 23 mg in Moderate to Severe Alzheimer's Disease," BMC Neurology, Biomed Central Ltd., London, GB, vol. 11, No. 1, May 25, 2011 (May 25, 2011), p. 57, XP021099938.
Center for Drug Evaluation and Research: "Application No. 022568; Medical Review(s)," Jul. 23, 2010 (Jul. 23, 2010), p. 1-94, XP002725060, retrieved from the internet: URL: http://www.accessdata.fda.gov/drugsatfda_docs/nda/2010-022568origls000medr.pdf [retrieved on May 15, 2014].
Gauthier: "Cholinergic adverse effects of cholinesterase inhibitors in Alzheimer's disease: epidemiology and management", Drugs & Aging, ADIS International Ltd, NZ, vol. 18, No. 11, Jan. 1, 2001 (Jan. 1, 2001), pp. 853-862, XP009136420.
Jackson Stephen et al.: "The safety and tolerability of donepezil in patients with Alzheimer's disease", British Journal of Clinical Pharmacology, vol. 58 Suppl. 1 Nov. 2004 (Nov. 2004), pp. 1-8, XP055120544.
Singer et al.: "Nightmares in patients with Alzheimer's disease caused by donepezil ; Therapeutic effect depends on the time of intake", Der Nervenarzt ; Organ Der Deutschen Gesellschaft Fur Psychiatric, Psychotherapie and Nervenheilkunde Organ Der Deutschen Gesellschaft Fur Neurologie, Springer, Berlin, DE, vol. 76, No. 9, Sep. 1, 2005 (Sep. 1, 2005), pp. 1127-1129, XP019321231.

* cited by examiner

*Primary Examiner* — Susan T Tran
(74) *Attorney, Agent, or Firm* — Merchant & Gould P.C.

(57) ABSTRACT

A timed release pharmaceutical composition comprising donepezil is provided, wherein the composition exhibits the in vitro dissolution profile when tested in a Paddle dissolution apparatus at 50 rpm in 900 ml 6.8 buffer at 37° C., less than about 20% w/w of donepezil is released in 3 to 6 hrs, and more than 90% w/w of donepezil is released after 12 hrs.

27 Claims, No Drawings

PHARMACEUTICAL COMPOSITIONS OF DONEPEZIL HAVING SPECIFIC IN VITRO DISSOLUTION PROFILE OR PHARMACOKINETICS PARAMETERS

This application is a National Stage Application of PCT/IB2014/059298, filed 27 Feb. 2014, which claims benefit of Serial No. 990/KOL/2012, filed 28 Feb. 2013 in India and which applications are incorporated herein by reference. To the extent appropriate, a claim of priority is made to each of the above disclosed applications.

FIELD OF THE INVENTION

The present invention relates to a timed release pharmaceutical composition of donepezil wherein the composition provides a plasma donepezil concentration profile that corresponds with the circadian rhythm of the acetylcholine (Ach) levels in the brain. The composition reduces the incidence of sleep disturbances which include difficulty in falling asleep, multiple awakenings during sleep, nightmares, disrupted sleep-wake rhythms, and early morning awakenings and also reduce the incidence of sundowning effect observed in subjects suffering from Alzheimer's disease. The composition, upon oral administration provides reduced incidence of gastrointestinal (GI) side effects.

BACKGROUND

Donepezil, known chemically as (±)-2,3-dihydro-5,6-dimethoxy2-[[1-(phenylmethyl)-4-piperidinyl]methyl]-1H-inden-1-one, is a reversible inhibitor of the enzyme acetylcholinesterase. It is currently available in tablet dosage forms of 5 mg, 10 mg and 23 mg doses under the trade name Aricept® or Aricep® or as orally disintegrating tablets (Aricept® ODT). Aricept® 23 mg film-coated tablet is a sustained-release formulation. Donepezil is indicated for the treatment of dementia of the Alzheimer's type with efficacy established in mild, moderate and severe Alzheimer's disease.

Alzheimer's disease (AD) is an age-related neurodegenerative disorder that is characterized by progressive loss of memory and deterioration of higher cognitive functions. In addition to its traditional symptomatology of deficits in cognitive function and memory, AD is characterized by a marked alteration in circadian rhythmicity, beyond that which is associated with ageing. In AD patients, the sleep-wake cycle is more disrupted than in healthy individuals and this can exacerbate behavioral disorders and memory dysfunction.

The sleep-wake cycle comprises three main phases: wakefulness, non-rapid eye movement (NREM) sleep and rapid eye movement (REM) sleep. On the basis of the depth of sleep, NREM sleep is subdivided into stages. In healthy young adults, sleep usually begins at the lightest stage, NREM stage 1, and progresses through stage 2 and into the deepest sleep states, stage 3 and stage 4, also known as delta or slow-wave sleep. The sleeper then progresses back to lighter sleep and then into REM sleep. In healthy individuals, a typical 8-hour period of sleep contains four or five cycles of these alternating sleep phases, with occasional brief awakenings. REM sleep accounts for 20-25% of total sleep time in most human adults.

It is well known that nightmares occur during the REM phase of sleep. The existing donepezil treatment increases the REM sleep percentage and hence causes nightmares.

Sleep disturbances are common in persons with AD. These sleep disturbances include difficulty in falling asleep, multiple awakenings during sleep, disrupted sleep-wake rhythms, and early morning awakenings. Sleep disturbances in persons with AD are a physical and psychological burden for their caregivers and are a major reason why such patients are admitted to long-term care institutions.

ACh plays an important role in maintaining a normal sleep pattern, which is important for memory consolidation. In the brain, ACh is thought to be released from cholinergic neurons according to a circadian rhythm. The cholinergic system is regulated for increased transmission during waking and motor activity and decreased transmission, in general, during sleep, with brief localized increases during REM sleep. The elements of the cholinergic system—synaptic ACh, stored ACh, acetylcholinesterase activity and cholinergic receptors—are coordinated to achieve this end. These rhythms may deteriorate with ageing and is a particular problem in AD.

Behavioral disturbances, such as nocturnal delirium, agitation or wandering are noticeable in older adults with AD and are believed to be associated with disrupted biological rhythms. This phenomenon is called "sundowning" which is a constellation of increasing behavioral disturbances in patients with dementia in the late afternoon or early evening. Sundowning represents an understudied area and the neurobiological basis of this behavioral pattern remains unspecified. One study demonstrates that this behavioral pattern coincides with time-dependent changes in basal forebrain acetylcholinesterase expression.

There exists a need to develop compositions of donepezil which provides reduced incidence of sleep disturbances, which include difficulty in falling asleep, multiple awakenings during sleep, disrupted sleep-wake rhythms and early morning awakenings. There also exists a need to develop compositions of donepezil which reduces the incidence of sundowning. These objectives can be achieved by formulating compositions which release donepezil in a pattern which corresponds with the circadian rhythm of the acetylcholine release from the cholinergic neurons.

The immediate release composition of donepezil results in a spike in the subject's blood plasma levels within 2 to 5 hours after administration of the drug. Following oral dosing, peak plasma concentration is achieved for Aricept® or Aricep® 10 mg, in approximately 3 hours. This initial spike in blood plasma levels causes undesirable side effects in subjects, such as anxiety, nightmares, insomnia, and/or gastrointestinal problems such as nausea, vomiting and diarrhea.

Prior art discloses sustained release compositions as a solution for reducing the incidence of these side effects.

U.S. Patent Application 2005/0232990 discloses a sustained release formulation comprising amorphous donepezil or an amorphous pharmaceutically acceptable salt thereof and a pharmaceutically acceptable polymeric carrier, wherein the polymeric carrier maintains the active agent in substantially amorphous form.

U.S. Patent Applications 2006/0280789, 2007/0129402, 2006/0159753, 2009/0208579, and 2011/0045074 disclose orally administrable matrix type sustained release formulations comprising a basic drug, an enteric polymer, and, optionally, one or more compounds selected from water-insoluble polymers, water-soluble sugars, sugar alcohols, and pharmaceutically acceptable excipients.

U.S. Patent Applications 2008/0213368 and 2010/0152164 disclose pharmaceutical compositions containing an anti-dementia drug and sustained-release base, with storage stability of the anti-dementia drug, wherein a high molecular weight acidic substance is added for stabilizing the anti-dementia drug.

PCT Application WO 2011/069076 discloses a sustained release tablet formulation comprising donepezil or a pharmaceutically acceptable salt thereof, further comprising at least one release rate controlling material that is a hydrophilic material, hydrophobic material, enteric polymer, or any combination thereof.

U.S. Patent Application 2011/0218216 discloses an extended-release pharmaceutical composition for an oral administration comprising donepezil or pharmaceutically acceptable salt thereof, a release-controlling agent and a microenvironment pH modifier.

U.S. Patent Application 2011/0237623 discloses a sustained-release formulation for an acetylcholinesterase inhibitor, comprising an acetylcholinesterase inhibitor and at least two gel-forming polymers.

However, the label of Aricept® or Aricep® discloses that the gastrointestinal side effects (nausea, vomiting and diarrhea), when they occur, appear more frequently with the 10 mg/day dose than with the 5 mg/day dose and more frequently with the 23 mg dose (sustained release formulation) than with the 10 mg dose. Specifically, in a controlled trial that compared a dose of 23 mg/day to 10 mg/day in patients who had been treated with donepezil 10 mg/day for at least three months, the incidence of nausea in the 23 mg group was markedly greater than in the patients who continued on 10 mg/day (11.8% vs. 3.4%, respectively), and the incidence of vomiting in the 23 mg group was markedly greater than in the 10 mg group (9.2% vs. 2.5%, respectively). The percent of patients who discontinued treatment due to vomiting in the 23 mg group was markedly higher than in the 10 mg group (2.9% vs. 0.4%, respectively).

Public Citizen, representing more than 225,000 members and supporters nationwide, had petitioned to the US FDA in June 2011 to immediately remove the 23 mg dose of Aricept® from the market because the 23 mg dose of Aricept® failed to meet the two efficacy criteria required by FDA as a condition of approval of drugs for dementia, and because the 23 mg dose of Aricept® significantly increased adverse events compared to the previously approved 10 mg dose, including increased risks for nausea, vomiting, diarrhea, anorexia, and confusion.

Hence, there is still a need for developing compositions of donepezil which provide a reduced incidence of undesirable gastrointestinal side effects in subjects, which include nausea, vomiting and diarrhea.

SUMMARY OF THE INVENTION

In an embodiment a timed release pharmaceutical composition of donepezil, provides a plasma donepezil concentration profile that corresponds with the circadian rhythm of the ACh levels in the brain.

In another embodiment the composition provides reduced incidence of sleep disturbances, which include difficulty in falling asleep, multiple awakenings during sleep, disrupted sleep-wake rhythms, and early morning awakenings.

In another embodiment the composition upon oral administration provides reduced incidence of sundowning.

In yet another embodiment the composition upon oral administration provides reduced incidence of gastrointestinal side effects selected from the group of symptoms consisting of nausea, vomiting and diarrhea.

In another embodiment, the composition exhibits an in vitro dissolution profile, wherein less than about 20% w/w of donepezil is released in 6 hours in 900 ml 0.1N HCl; wherein less than about 20% w/w of donepezil is released in 3 to 6 hours in 900 ml pH 6.8 phosphate buffer; about 20 to 90% w/w, preferably about 20 to 85% w/w of donepezil is released in 6 to 12 hours in 900 ml pH 6.8 phosphate buffer and more than about 90% w/w of donepezil is released after 12 hours in 900 ml pH 6.8 phosphate buffer.

In yet another embodiment, the single dose $AUC_{(2-10)}$ of the composition is 40% to 95%, or 55 to 95%, or preferably 40% to 80%, or preferably 45% to 85%, preferably 65% to 85%, or preferably 70% to 80% less than the single dose $AUC_{(2-10)}$ of an immediate release composition of donepezil, wherein both the compositions have equivalent dose of donepezil and are administered orally at night.

In yet another embodiment, the steady state $AUC_{(2-10)}$ of the composition is 5% to 35%, preferably 10% to 30%, and most preferably 10% to 20% less than the steady state $AUC_{(2-10)}$ of an immediate release composition of donepezil, wherein both the compositions have equivalent dose of donepezil and are administered orally at night.

In yet another embodiment, the single dose $AUC_{(19-22)}$ of the composition is 10% to 50%, preferably 15% to 45%, more preferably 20% to 40%, and most preferably 25% to 35% more than the single dose $AUC_{(19-22)}$ of an immediate release composition of donepezil, wherein both the compositions have equivalent dose of donepezil and are administered orally at night.

In yet another embodiment, the steady state $AUC_{(19-22)}$ of the composition is 10% to 100%, preferably 50% to 100%, preferably 60% to 100%, and most preferably 70% to 100% more than the steady state $AUC_{(19-22)}$ of an immediate release composition of donepezil, wherein both the compositions have equivalent dose of donepezil and are administered orally at night.

DETAILED DESCRIPTION OF THE INVENTION

The commercially available compositions of donepezil are at odds with the physiology of the cholinergic system, which is active during the day and quiescent at night. These compositions are so administered that they are active at the night and interfere with NREM sleep and promote REM sleep. This results in sleep disturbances in subjects treated with donepezil.

Further, sundowning syndrome is noticeable in older adults with AD and is believed to be associated with disrupted biological rhythms. Some studies have suggested that increase in acetylcholinesterase is responsible for this phenomenon.

The specification discloses a timed release pharmaceutical composition of donepezil, which provides a plasma donepezil concentration profile that corresponds with the circadian rhythm of the ACh levels in the brain. The release of donepezil from the composition is such that it provides lower levels of donepezil at night and higher levels of donepezil during daytime when compared to the commercially available compositions of donepezil (Aricept® or) Aricep®.

The pharmaceutical compositions of donepezil demonstrate similar or greater efficacy and also result in lower incidence of side effects as compared to the commercially available compositions of donepezil.

Definitions

The term "donepezil" includes various forms of donepezil such as pharmaceutically acceptable salt(s), hydrate(s), solvate(s), polymorph(s), isomer(s), stereoisomer(s), enantiomer(s), racemate(s), ester(s), prodrug(s), derivative(s), analogue(s), metabolite(s) and complex(es) thereof. Donepezil may be present from 0.5 to 90% w/w, preferably 1 to 50% w/w and more preferably 1.5 to 25% w/w of the total weight of the composition.

The term "pharmaceutically acceptable salt" means a salt which is acceptable for administration to a subject, such as a mammal (e.g., salts having acceptable mammalian safety for a given dosage regime). Such salts can be derived from pharmaceutically acceptable inorganic or organic bases and from pharmaceutically acceptable inorganic or organic acids. The preferred salt is donepezil hydrochloride (HCl).

The term "timed release pharmaceutical composition" refers to a composition which is designed to release specific amounts of donepezil in set periods of time such that the resulting plasma donepezil concentration profile in the subject simulates the circadian rhythm of ACh levels in the brain. The release of donepezil is delayed by about 2 to 6 hours after administration followed by release of more than 90% of donepezil 12 hours after administration.

The term "dissolution profile" refers to a plot of the cumulative amount of active ingredient released as a function of time. The dissolution profile is characterized by the test conditions selected. Thus the dissolution profile can be generated at a preselected apparatus type, shaft speed, temperature, volume, and pH of the dissolution media. The dissolution apparatus can be selected from the basket type or the paddle type. The shaft speed can be 100 rotations per minute (RPM) for the basket type apparatus and can be selected from 50 to 75 RPM for the paddle type apparatus. Decreasing or increasing the shaft speed in the range of 25 to 150 RPM can be justified if supported by the dissolution data obtained. The temperature should be 37° C. The volume of the apparatus can be selected from 500 mL to 1000 mL, most preferably 900 mL. The dissolution media used are dilute HCl (0.1N), buffers in the pH range 1.2-6.8, simulated gastric or intestinal fluid and water.

"Circadian rhythm" is the regular 24 hours rest/wake pattern seen in normal individuals. ACh levels in the brain also follow a circadian rhythm wherein there are increased ACh levels during waking and motor activity and decreased levels, in general, during sleep.

The sleep-wake cycle or rhythms comprises three main phases: wakefulness, non-rapid eye movement (NREM) sleep and rapid eye movement (REM) sleep. On the basis of the depth of sleep, NREM sleep is subdivided into stages. In healthy young adults, sleep usually begins at the lightest stage, NREM stage 1, and progresses through stage 2 and into the deepest sleep states, stage 3 and stage 4, also known as delta or slow-wave sleep. The sleeper then progresses back to lighter sleep and then into REM sleep. In healthy individuals, a typical 8-hour period of sleep contains four or five cycles of these alternating sleep phases, with occasional brief awakenings. REM sleep accounts for 20-25% of total sleep time in most human adults.

Sleep stages are identified by using an electroencephalogram to detect the electrical activity in the cerebral cortex, an electrooculogram to monitor eye movements, and an electromyogram to measure muscle activity. The combination of these three recordings is referred to as polysomnography.

Sleep quality is defined by the nighttime sleep characteristics revealed by self-report or polysomnography. It usually includes sleep onset latency, waking frequency, durations of awakening after sleep onset, amount of nighttime sleep, and sleep efficiency.

"Sleep onset latency time" refers to the length of time that it takes to accomplish the transition from full wakefulness to sleep, normally to the lightest of the non-REM sleep stages.

"REM sleep cycles" refers to the number of times the sleeper enters into the REM phase of sleep cycle during a normal nighttime sleep.

"REM phase duration" refers to amount of time the sleeper remains in the REM phase during a normal nighttime sleep.

"Sleep efficiency" refers to the ratio of the time a sleeper is asleep to the time the sleeper spends in the bed.

"Parasomnia" refers to a category of sleep disorders that involve abnormal and unnatural movements, behaviors, emotions, perceptions, and dreams that occur while falling asleep, sleeping, between sleep stages, or during arousal from sleep. Most parasomnias are dissociated sleep states which are partial arousals during the transitions between wakefulness and NREM sleep, or wakefulness and REM sleep.

"REMS parasomnia" refers to a category of sleep disorders that involve abnormal and unnatural movements, behaviors, emotions, perceptions, and dreams that occur during the REM phase of sleep.

"REM sleep behavior disorder" is a sleep disorder (parasomnia) that involves abnormal behavior during the REM sleep. In a person with REM sleep behavior disorder (RBD), the paralysis that normally occurs during REM sleep is incomplete or absent, allowing the person to "act out" his or her dreams. RBD is characterized by the acting out of dreams that are vivid, intense, and violent. Dream-enacting behaviors include talking, yelling, punching, kicking, sitting, jumping from bed, arm flailing, and grabbing.

"Sundowning" is the appearance or exacerbation of behavioral disturbances associated with the afternoon and/or evening hours in subjects suffering from Alzheimer's. Individual behavioral components of the condition which is frequently termed sundowning in subjects suffering from Alzheimer's may include anxiety, agitation, locomotor activity, delirium, carphologic behavior (restlessness), escape behaviors, expression of feelings, talking and other verbalizations, appearance of searching, combativeness, purposeless movement, wandering, loud/prolonged incoherent vocalization, hallucinations, confusion, disorientation, restraint removal, searching, tapping or banging etc. These behaviors usually start at around 4 PM and last as late as 11 PM.

The timed release pharmaceutical composition of donepezil can be characterized by its pharmacokinetic (pK) parameters which describes the in vivo characteristics of donepezil over time. These pK parameters include $C_{max}$, $T_{max}$, AUC, $AUC_{(X-Y)}$.

$C_{max}$ is the "maximum plasma concentration" which is defined as the concentration of donepezil in the plasma at the point of maximum concentration.

"$T_{max}$" refers to the time at which the concentration of donepezil in the plasma is the highest.

The term "AUC" as used herein means "area under the curve" in a plot of concentration of drug in plasma versus time from ingestion. AUC is usually given for the time interval zero to any time 't' post drug administration or extrapolated to infinity. AUC zero to infinity is estimated based on mathematical approaches using limited number of concentration measurements.

"$AUC_{(X-Y)}$" is the "area under the curve" in a plot of concentration of drug in plasma versus time, measured from time point X hours after administration of the composition to time point Y hours after administration of the composition.

The pK parameters can be measured after administration of a single dose of the composition or after administration of multiple doses of the composition such that steady state of donepezil is attained.

"Single dose $AUC_{(X-Y)}$" relates to the $AUC_{(X-Y)}$ which is measured after administration of a single dose of the composition. "Steady state $AUC_{(X-Y)}$" relates to the $AUC_{(X-Y)}$ which is measured after administration of the composition on a daily basis for at least 14 days.

"Immediate release" refers to a conventional or non-modified release composition, in which greater than or equal to about 75% of the active agent is released within 45 minutes of administration, preferably within 30 minutes of administration.

"Rescue anti-acid drugs" refer to use of anti-acid drugs such as proton pump inhibitors (PPIs), histamine 2 receptor antagonists (H2RAs) or antacids to manage GI side-effects which become persistent or which recur or which get worse on donepezil therapy.

"Titration period" refers to a time period required for gradually adjusting the dose of a medication to reach the optimum therapeutic dose with acceptable tolerability.

"Commercially available compositions of donepezil" comprises of immediate release and sustained release compositions of donepezil available under the tradename ARICEPT®.

The "immediate release composition of donepezil" include "ARICEPT® OR ARICEP®" film coated tablets, comprising 5 & 10 mg of donepezil hydrochloride, and inactive ingredients containing lactose monohydrate, cornstarch, microcrystalline cellulose, hydroxypropyl cellulose, and magnesium stearate. The film coating contains talc, polyethylene glycol, hydroxypropyl methylcellulose, and titanium dioxide. The 10 mg tablet further includes yellow iron oxide as a coloring agent. The immediate release composition of donepezil attains $T_{max}$ 2 to 5 hours after single dose administration.

The "sustained release composition of donepezil" includes "ARICEPT®" film coated tablets comprising 23 mg of donepezil hydrochloride and inactive ingredients containing ethylcellulose, hydroxypropyl cellulose, lactose monohydrate, magnesium stearate and methacrylic acid copolymer, Type C. The film coating includes ferric oxide, hypromellose 2910, polyethylene glycol 8000, talc and titanium dioxide. The sustained release composition of donepezil attains $T_{max}$ 8 hours after single dose administration.

In an embodiment, the timed release pharmaceutical composition of donepezil exhibits an in vitro dissolution profile wherein less than about 20% w/w of donepezil is released in 6 hours in 900 ml 0.1N HCl; wherein less than about 20% w/w of donepezil is released in 3 to 6 hours in 900 ml pH 6.8 phosphate buffer; about 20 to 90% w/w, preferably about 20 to 85% w/w of donepezil is released in 6 to 12 hours in 900 ml pH 6.8 phosphate buffer and more than about 90% w/w of donepezil is released after 12 hours in 900 ml pH 6.8 phosphate buffer.

In another embodiment, the single dose $AUC_{(2-10)}$ of the composition is 40% to 95%, or 55 to 95%, or preferably 40% to 80%, or preferably 45% to 85%, preferably 60% to 90%, or preferably 65% to 85%, preferably 70% to 80% less than the single dose $AUC_{(2-10)}$ of an immediate release composition of donepezil, wherein both the compositions have equivalent dose of donepezil and are administered orally at night.

In yet another embodiment, the steady state $AUC_{(2-10)}$ of the composition is 5% to 35%, preferably 10% to 30%, and most preferably 10% to 20% less than the steady state $AUC_{(2-10)}$ of an immediate release composition of donepezil, wherein both the compositions have equivalent dose of donepezil and are administered orally at night.

In yet another embodiment, the single dose $AUC_{(19-22)}$ of the composition is 10% to 50%, preferably 15% to 45%, more preferably 20% to 40%, and most preferably 25% to 35% more than the single dose $AUC_{(19-22)}$ of an immediate release composition of donepezil, wherein both the compositions have equivalent dose of donepezil and are administered orally at night.

In yet another embodiment, the steady state $AUC_{(19-22)}$ of the composition is 10% to 100%, preferably 50% to 100%, preferably 60% to 100%, and most preferably 70% to 100% more than the steady state $AUC_{(19-22)}$ of an immediate release composition of donepezil, wherein both the compositions have equivalent dose of donepezil and are administered orally at night.

These pK parameters of the composition are compared to those of an immediate release composition of donepezil, preferably between compositions containing similar dose of donepezil.

In an embodiment pK parameters of the composition are also compared to the commercially available sustained release composition comprising 23 mg of donepezil hydrochloride (Aricept®).

In another embodiment, the pK parameters of the composition are also compared to commercially available compositions of donepezil wherein the compositions have different doses of donepezil. In such cases, the dose corrected partial AUC is measured. The dose corrected partial AUC is the partial AUC divided by the number of milligrams of donepezil in the formulation. The timed release pharmaceutical composition of donepezil provides a plasma donepezil concentration profile that corresponds with the circadian rhythm of the ACh levels in the brain.

In an embodiment, the composition reduces incidence of sleep disturbances, which includes difficulty in falling asleep, multiple awakenings during sleep, disrupted sleep-wake rhythms, and early morning awakenings.

In another embodiment the composition upon oral administration provides, reduced incidence of insomnia and nightmares and reduced sleep onset latency time. It reduces REM sleep cycles, REM phase duration, waking frequencies and the durations of awakening after sleep onset; prolongs the nighttime sleep duration, improves sleep efficiency, provides reduced incidence of REMS parasomnia and provides reduced incidence of behavioral and motor disturbances in the REM sleep behavior disorder.

In another embodiment, the composition upon oral administration provides reduced incidence of sundowning.

In yet another embodiment, the composition upon oral administration provides reduced incidence of gastrointestinal side effects selected from the group consisting of nausea, vomiting and diarrhea. The composition reduces the need for use of rescue anti-acid drugs in subjects being treated with donepezil.

In another embodiment, the composition shortens the titration period required for donepezil administration. Preferably, the composition shortens the titration period required for donepezil administration by two to four weeks.

In another embodiment, the composition is used to treat a subject suffering from a disease or a condition characterized by symptoms of dementia and/or cognitive impairments. Such disease or condition can be selected from the group consisting of Alzheimer's disease, mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, amyotrophic lateral sclerosis, Huntington's disease, cognitive deficits associated with traumatic brain injury (TBI), cognitive and sensorimotor gating deficits associated with schizophrenia, cognitive deficits associated with bipolar disorder, cognitive impairments associated with depression, delirium, schizoaffective disorder, aphasia, autism, schizophreniform disorder, obstructive sleep apnea, sleep deprivation, cerebrovascular accident, relapsing remitting multiple sclerosis, ischemic stroke, anxiety disorder.

Preferably, the composition is used to treat a subject suffering from mild, moderate or severe Alzheimer's disease.

The timed release pharmaceutical composition of donepezil comprises donepezil in an amount selected from 3 mg to 50 mg, from 5 mg to 25 mg, from 10 mg to 25 mg, from 7 mg to 18 mg. In an embodiment, the pharmaceutical composition comprises 3 mg, 4 mg, 5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 17.5 mg, 18 mg, 18.5 mg, 19 mg, 20 mg or 23 mg of donepezil.

In one of the embodiment the timed release pharmaceutical composition provides dose reduction from about 5-50%, preferably 10-45%, preferably, 15-40% of the standard dose (5 mg, 10 mg and 23 mg) without reducing the efficacy.

The dosage regimen for treating and preventing the diseases described herein with donepezil can be selected in accordance with a variety of factors, including the age, weight, sex, and medical condition of the subject, the route of administration, pharmacological considerations such as the activity, efficacy, pharmacokinetic and toxicology profiles of the active ingredient, and whether a drug delivery system is used. The doses can be administered in one to four portions over the course of a day, preferably once a day.

In an embodiment, the timed release pharmaceutical composition of donepezil may be administered in two portions over the course of a day, wherein the amount of donepezil present in the two portions is same or different. Preferably, the amount of donepezil present in the two portions is different and wherein the portion administered in the night has a greater amount of donepezil than the portion administered in the morning. In a preferred embodiment, the pharmaceutical composition of donepezil comprising 16 mg, 17 mg, 17.5 mg, 18 mg or 18.5 mg of donepezil is administered in the night and pharmaceutical composition of donepezil comprising 6.5 mg, 7 mg, 7.5 mg, 8 mg, 8.5 mg or 9 mg of donepezil is administered in the morning.

The term active ingredient, active agent and drug herein can be interchangeably used.

The composition can be administered to the subject in the morning or in the evening or night. Preferably, the composition is administered in the evening or night. Preferably the composition is administered between 8 p.m. and 12 a.m. and more preferably, the composition is administered between 9 p.m. and 11 p.m. or just before going to sleep at night.

The composition is particularly suitable for oral administration. The composition include but is not limited to tablets (single layered tablets, multilayered tablets, mini tablets, bioadhesive tablets, caplets, matrix tablets, tablet within a tablet, mucoadhesive tablets, gastroretentive tablets), pellets, beads, granules, capsules, microcapsules, tablets in capsules and microspheres, matrix formulations, microencapsulation and powder/pellets/granules for suspension. In some embodiments, powders, pellets, and granules may be coated with a suitable polymer or a conventional coating material to achieve, for example, greater stability in the gastrointestinal tract, or to achieve the desired rate of release. Moreover, capsules containing a powder, pellets, or granules may be further coated. It may also include kits. Tablets are most preferably used.

In an embodiment, the composition comprises donepezil and one or more release controlling agent(s) to produce a timed release profile. The release controlling agent may be selected from hydrophilic or hydrophobic agents, which can be polymeric or non-polymeric and which are capable of modulating the rate of release of the active ingredient(s), which can be pH dependent or pH independent. The release controlling agent(s) may be natural, semisynthetic and synthetic agents or mixtures thereof. The release controlling agent can be used from about 1 to about 70% w/w, preferably about 5 to about 60% w/w, most preferably about 10 to about 50% w/w of the total composition.

The hydrophilic release controlling agents may be selected from hydroxyethylcellulose, hydroxypropyl cellulose, hydroxypropyl methylcellulose, sodium carboxymethyl cellulose, sodium alginate, carbomer (Carbopol™), xanthan gum, guar gum, locust bean gum, poly vinyl acetate, polyvinyl alcohol. Preferably the release-controlling agent is hydroxypropylmethylcellulose.

The hydrophobic release controlling agents may be selected from hydrogenated vegetable oil, purified grades of beeswax; fatty acids; long chain fatty alcohols, such as cetyl alcohol, myristyl alcohol, and stearyl alcohol; glycerides such as glyceryl esters of fatty acids like glycerylmonostearate, glyceryldistearate, glyceryl esters of hydrogenated castor oil and the like; oils such as mineral oil and the like, or acetylated glycerides; ethyl cellulose, stearic acid, paraffin, carnauba wax, talc; and the stearate salts such as calcium, magnesium, zinc and other materials known to one of ordinary skill in the art.

Natural release controlling agents may be selected from proteins (e.g., hydrophilic proteins), such as pectin, zein, modified zein, casein, gelatin, gluten, serum albumin, or collagen, chitosan, oligosaccharides and polysaccharides such as cellulose, dextrans, tamarind seed polysaccharide, gellan, carrageenan, xanthan gum, gum Arabic, guar gum, locust bean gum; hyaluronic acid, polyhyaluronic acid, alginic acid, sodium alginate or combinations thereof Synthetic release controlling agents may be selected from polyamides, polycarbonates, polyalkylenes, polyalkylene glycols such as poly(ethylene glycol), polyalkylene oxides, polyethylene oxide, polyalkylene terephthalates, polyvinyl alcohols (PVA), polyvinylphenol, polyvinyl ethers, polyvinyl esters, polyvinyl halides, polyvinylpyrrolidone (PVP), polyglycolides, polysiloxanes, polyurethanes, polystyrene, polylactides, poly(butyric acid), poly(valeric acid), poly (lactide-co-glycolide), poly(ethyleneterephthalate), poly (lactide-co-caprolactone), polyanhydrides (e.g., poly(adipic anhydride), polyorthoesters, poly(fumaric acid), poly(maleic acid), polyvinyl acetate, polystyrene; polymers of acrylic and methacrylic esters (available under the trade name Eudragit® like Eudragit® RSPO, Eudragit® RLPO, Eudragit® L100-55); carbomer, Carbopol®; celluloses and cellulose derivatives such as methyl cellulose (MC), ethyl cellulose (EC), hydroxypropyl cellulose (HPC), hydroxypropylmethyl cellulose (HPMC), hydroxybutylmethyl cellulose, hydroxyl ethyl cellulose (HEC) sodium carboxymethyl cellulose (Sod.CMC), cellulose acetate (CA), cellulose propionate, cellulose acetate butyrate, cellulose acetate phthalate (CAP), carboxymethyl cellulose, cellulose triacetate, cellulose sulfate sodium salt and blends and copolymers thereof or mixtures thereof.

The composition further comprises pharmaceutically acceptable excipients. Examples of pharmaceutically acceptable excipients may include diluents, binders, disintegrants, lubricants, glidants, and coloring agents. The amount of additive employed depends upon various factors such as amount of active agent to be used.

Diluents may be selected from alumina, starch, kaolin, polacrilin potassium, powdered cellulose, microcrystalline cellulose, sugars such lactose, glucose, fructose, sucrose, mannose, dextrose, galactose, dextrates, dextrin; sugar alcohols such as mannitol, sorbitol, xylitol, lactitol, starch, calcium carbonate, calcium phosphate dibasic or tribasic, calcium sulphate or combinations thereof.

Binders may be selected from starches such as potato starch, wheat starch, corn starch; microcrystalline cellulose such as products known under the registered trademarks Avicel, Filtrak, Heweten or Pharmacel; celluloses such as HPC, HEC, HPMC, EC, sodium carboxy methyl cellulose; natural gums like *acacia*, alginic acid, guar gum; liquid glucose, dextrin, povidone, syrup, polyethylene oxide, PVP, poly-N-vinyl amide, polyethylene glycol, gelatin, poly propylene glycol, tragacanth, combinations thereof and other materials known to one of ordinary skill in the art and mixtures thereof.

Disintegrants may be selected from low-substituted hydroxypropyl cellulose, e.g. L-HPC; cross-linked polyvinyl pyrrolidone (PVP-XL), e.g. Kollidon® CL and Polyplasdone® XL; cross-linked sodium carboxymethylcellulose, e.g. Ac-di-sol®, Primellose; sodium starch glycolate, e.g. Primojel®; sodium carboxymethylcellulose; sodium carboxymethyl starch, e.g. Explotab®; ion-exchange resins, e.g. Dowex® or Amberlite®; microcrystalline cellulose, e.g. Avicel®; starches and pregelatinized starch, e.g. Starch 1500®, Sepistab ST200®; formalin-casein, e.g. Plas-Vita® and combinations thereof.

Lubricants may be selected from those conventionally known in the art such as magnesium, aluminum or calcium or zinc stearate, silicon oxide, polyethylene glycol, glycerylbehenate, mineral oil, talc, sodium stearylfumarate, stearic acid, vegetable oil such as hydrogenated vegetable oil and combinations thereof.

Glidants may be selected from silicon dioxide; magnesium trisilicate, talc and tribasic calcium phosphate, calcium silicate, magnesium silicate, colloidal silicon dioxide, silicon hydrogel.

Coloring agents may be selected from ferric oxide; pigments such as titanium dioxide. Colorants can also include natural food colors and dyes suitable for food, drug and cosmetic applications.

The amount of each type of excipient employed, e.g. glidant, binder, disintegrant, filler or diluent and lubricant may vary. Thus for example, the amount of glidant may vary within a range of 0.1 to 10% by weight, in particular 0.1 to 5% by weight, e.g. 0.1 to 0.5% by weight; the amount of binder may vary within a range of from about 0.5 to 45% by weight, e.g. 20 to 30% by weight; the amount of disintegrant may vary within a range of from 0.5 to 5% by weight, e.g. 1% by weight; the amount of filler or diluent may vary within a range of from 10 to 60% by weight; whereas the amount of lubricant may vary within a range of from 0.1 to 5.0% by weight.

One excipient can perform more than one function.

The composition can be prepared by various methods known in the art such as by dry granulation, wet granulation, melt granulation, direct compression, double compression, extrusion spheronization, layering and the like. The pharmaceutical composition can be in any shape and size. In an embodiment, the tablets are round with initial diameter of 13.3 mm.

In an embodiment, the process of making the composition comprises as described below:

i) blending donepezil and pharmaceutically acceptable additives,
ii) subjecting the blend to slugging/compaction to form a coprimate,
iii) converting the coprimate to granules,
iv) compressing the granules to form the solid oral dosage form, and
v) optionally coating the solid oral dosage form.

Compaction of the blend into coprimate may be carried out using a slugging technique or roller compaction. The milling of the granules may be carried out according to conventional milling methods.

The process of wet granulation includes aqueous or non-aqueous granulation. The wet granulation process comprises the admixing of the active ingredient with diluent(s) and/or rate controlling polymer, and granulation of the blend with the binder mass to form the wet mass followed by drying and sizing. The binder may optionally be admixed with the dry blend and granulation performed with aqueous or non-aqueous solvent. The solvent for the non-aqueous granulation is selected from ethanol, isopropyl alcohol and dichloromethane or mixtures thereof.

The composition may further, be coated with a functional or non-functional coating. The coating may comprise about 1% to about 40%, about 3% to about 30%, about 5% to about 25%, about 6% to about 10%, about 1% to about 10%, about 1% to about 5%, about 2% to about 10%, about 2% to about 8% of the total composition.

The coating materials for use in the embodiments disclosed herein includes, but is not limited to, natural, semi-synthetic and synthetic agents or combinations thereof.

The inclusion of an effective amount of a plasticizer in the coating may improve the physical properties of the coating. Generally, the amount of plasticizer included in a coating solution is based on the concentration of the polymer, e.g., most often from about 1 to about 50 percent by weight of the polymer. Concentrations of the plasticizer, however, can be determined by routine experimentation. Examples of plasticizers include plasticizers such as dibutylsebacate, phthalate esters such as diethyl phthalate, dibutyl phthalate, triacetin, acetylated monoglycerides, castor oil, citric acid esters such as triethyl citrate, tributyl citrate, 1,2-propylene glycol, polyethylene glycols, propylene glycol, acetin or combinations thereof.

Suitable methods can be used to apply the coating such as simple or complex coacervation, interfacial polymerization, liquid drying, thermal and ionic gelation, spray drying, spray chilling, fluidized bed coating, pan coating, electrostatic deposition, compression coating, hot melt (extrusion) coating. Such methods are well known to those skilled in the art.

The solvent may be selected alcoholic or hydroalcoholic. Alcoholic solvents may be selected from methanol, ethanol, isopropyl alcohol, halogenated hydrocarbons such as dichloromethane(methylene chloride), hydrocarbons such as cyclohexane, and acetone and combinations thereof.

In an embodiment, the composition is a coated composition, which comprises: a) a core comprising donepezil and one or more release controlling agent(s), and b) a functional coating comprising one or more release controlling agent(s).

In another embodiment, the composition is a multilayered composition comprising a controlled release layer and a gastroretentive layer. The controlled release layer comprises donepezil and one or more release controlling agent(s). The gastroretentive layer may be a bioadhesive layer and/or a swellable layer. The multilayered composition may further be coated with a functional coating comprising one or more release controlling agent(s).

Gastro retention of the pharmaceutical composition may be achieved by using swelling and expanding systems which are retained by virtue of size of the pharmaceutical composition that is more than the size of the pyloric sphincter e.g. Plug-Type systems. Preferably, the initial diameter of such compositions should be 13.3 mm. In this type of gastroretentive technique, release controlling agents imbibe water and swell enough to be retained in the upper part of the GIT.

In another embodiment, the composition is a multi-layered composition, wherein the composition is core-shell type in which the gastroretentive component and delayed controlled release component make a bilayer tablet as a core or a tablet-in-tablet as a core in which delayed controlled release component as inner core and gastroretentive component as outer core.

In yet another embodiment, the composition is an osmotically driven release system. With an osmotically driven release system, at least one, preferably all, surface(s) of the release system, preferably those which are in contact or which may come into contact with the release medium, are semi-permeable, preferably provided with a semi-permeable coating, so the surfaces are permeable to the release medium but substantially, and preferably completely, impermeable to the active ingredient, whereby the surface and/or optionally the coating comprises at least one opening for releasing the active ingredient. This is preferably taken to mean a system in tablet form with a delivery opening, an osmotic pharmaceutical composition core, a semi-permeable membrane and a polymeric part which exerts pressure. A useful example of such a system include in particular the OROS® systems such as Push-Pull® system, delayed Push-Pull® system, Multi-Layer Push-Pull® system, the Push-Stick System and in certain cases the L-OROS®. The other types of osmotic active ingredient delivery systems like elementary osmotic pump systems, controlled porosity osmotic pump systems, osmotic bursting osmotic pump systems, monolithic osmotic system, OROS-CT can also be used to achieve a slow release.

In another embodiment, the composition can be a bioadhesive or mucoadhesive composition, wherein the composition can be retained in any part of the gastrointestinal tract (GIT) for increasing the GIT residence time, to increase the exposure of the composition to the GIT thus facilitating extended period of absorption of the active ingredient. Bioadhesive and mucoadhesive can be used interchangeably.

Animal Studies

The effect of the composition in reducing the incidence of sundowning effect can be demonstrated using animal studies with aged mice or amyloid precursor protein (APP) transgenic mice or other appropriate animal species. The following endpoints may be measured at different time points of light and dark cycle:

a) Behavioral parameters indicating sundowning:
   Anxiety-like behavior
   Locomotor activity
b) AChE levels measurement
c) Body temperature measurement Clinical Studies I. Single-Dose and Steady State Cross Over PK Study AUC Results (Donepezil Formulation of Present Invention Administered Night-Time Versus Donepezil IR Night-Time)

The results of Single-dose and steady state cross over PK study AUC results (Donepezil formulation of present invention administered night-time Versus Donepezil IR administered Night-Time) are disclosed in Table 1.

TABLE 1

AUC differences: Donepezil formulation of present invention administered night-time Versus Donepezil IR Night-Time

|  | Donepezil IR-night-time | Donepezil formulation of present invention-Night-time |
|---|---|---|
| AUC2-10 (Single dose) | 72 | 5 |
| % Difference |  | −93.0* |
| AUC19-22 (Steady state) | 52 | 104 |
| % Difference |  | +100.0* |

*(minus (−) sign indicates lower AUC; (+) sign indicates higher value) than Donepezil IR.

II. Polysomnography Studies:

Two studies were carried out to compare effects of Donepezil 10 mg (prepared according to present invention) versus Donepezil IR 10 mg (Aricep® marketed by Eisai) and versus placebo on REM sleep in healthy human subjects Both the studies consisted of a screening visit for eligibility check followed by assessment and dosing visits in period 1 and period 2. Period 1 also consisted of an adaptation night during which each subject was instructed to sleep in the recording room on the first night to allow for adaptation and baseline Nocturnal Polysomnography (NPSG) recordings followed by the second night for dosing. All randomized subjects received single dose of each study drug separated by an adequate wash-out period. Each eligible subject was given Actisleep, a small, wrist-worn actigraphy-based data logger to assess rest activity and sleep patterns for last 7 days before dosing in each period. ActiLife 6 data analysis software was used to assess the Actisleep data.

The sleep parameters recorded for assessment were REM sleep time, REM sleep latency, % REM sleep, Sleep latency, Sleep efficiency index, Sleep period time, Time awake, Time spent in sleep stage 1, stage 2 and stage 3 sleep and Total sleep time. Sleep recordings were made using the Alice 5® computerised polysomnographic system.

In each study, the study drugs were given to each randomized subject as a single dose at 22.30 hours of the dosing night in each period. NPSG recordings were started immediately after dosing and ended when subject woke-up next morning, either by spontaneous arousal or till 8 A.M, if no spontaneous arousal occurred.

The results of the study of Donepezil formulation of present invention vs placebo are summarized in table 2, and Donepezil formulation of present invention vs Donepezil IR are summarized in Table 3.

TABLE 2

Comparison Donepezil formulation of present invention versus placebo on of sleep parameters

| Sleep Parameters | Donepezil formulation of present invention (Mean ± SE) | Placebo (Mean ± SE) | P-value* |
|---|---|---|---|
| REM sleep time (min) | 116.5 ± 11.98 | 113.5 ± 14.07 | 0.7864 |
| REM sleep latency (min) | 109.75 ± 29.49 | 137.5 ± 31.68 | 0.2768 |
| % REM sleep | 0.27 ± 0.03 | 0.26 ± 0.03 | 0.5505 |
| Sleep latency (min) | 3.63 ± 1.50 | 12.19 ± 4.75 | 0.0632 |
| Sleep efficiency index | 0.93 ± 0.01 | 0.93 ± 0.01 | 0.8857 |
| Sleep period time (min) | 459 ± 19.06 | 465.5 ± 20.52 | 0.5979 |
| Time awake (min) | 24.81 ± 4.82 | 19.0 ± 4.21 | 0.3977 |
| Time spent in sleep stage 1 (min) | 1.88 ± 0.25 | 1.81 ± 0.35 | 0.8505 |
| Time spent in sleep stage 2 (min) | 149.88 ± 12.66 | 148.06 ± 15.17 | 0.8085 |
| Time spent in sleep stage 3 (min) | 157.75 ± 14.66 | 169.69 ± 16.05 | 0.3301 |
| Total sleep time (min) | 425.75 ± 17.67 | 433 ± 20.69 | 0.5988 |

*Paired t-test

Comparison between modified release donepezil formulation of present invention versus placebo in terms of changes in sleep parameters. It can be observed that there was no significant difference (P>0.05) between the groups in terms of REM sleep time, REM sleep latency, % REM sleep, Sleep latency, Sleep efficiency index, Sleep period time, Time awake, Time spent in sleep stage 1, stage 2 and stage 3 sleep and Total sleep time. None of the subjects reported nightmares or difficulty in falling asleep after dosing. Thus the study showed that there is no prolongation of REM sleep time with Donepezil formulation of present invention compared to placebo.

TABLE 3

Effects of Treatment with Donepezil formulation of present invention and Donepezil IR on Baseline Sleep Parameters

| Sleep Parameters | Baseline (N = 8) Mean ± SE | Donepezil 10 mg formulation of present invention | | Donepezil IR (10 mg) | |
|---|---|---|---|---|---|
| | | Post-Dose (N = 8) Mean ± SE | P-value* | Post-Dose (N = 8) Mean ± SE | P-value* |
| REM Sleep time (min) | 79.75 ± 10.46 | 93.5 ± 13.84 | 0.22 | 119.94 ± 13.53 | 0.01 |
| REM Sleep latency (min) | 128.56 ± 24.67 | 129.69 ± 23.65 | 0.93 | 127.06 ± 21.49 | 0.95 |
| % REM Sleep | 19 ± 2 | 23 ± 3 | 0.23 | 30 ± 3 | 0.01 |
| Sleep latency (min) | 25.25 ± 13.86 | 9.13 ± 2.69 | 0.30 | 16.13 ± 6.47 | 0.60 |
| Sleep Efficiency Index (%) | 84 ± 3 | 89 ± 2 | 0.15 | 86 ± 2 | 0.52 |
| Sleep period time (min) | 485.75 ± 16.59 | 456.38 ± 17.36 | 0.21 | 468.38 ± 7.84 | 0.25 |
| Time Awake (min) | 46.25 ± 15.03 | 39.69 ± 10.41 | 0.67 | 38.69 ± 9.67 | 0.69 |
| Time spent in sleep stage 1 (min) | 4.69 ± 1.17 | 6.44 ± 1.59 | 0.35 | 2.81 ± 1.15 | 0.21 |
| Time spent in sleep stage 2 (min) | 162.44 ± 16.87 | 165.13 ± 16.27 | 0.90 | 129.44 ± 16.83 | 0.04 |
| Time spent in sleep stage 3 (min) | 162.25 ± 19.37 | 141.5 ± 14.39 | 0.13 | 151.13 ± 10.50 | 0.47 |
| Total sleep time (min) | 408.81 ± 20.73 | 406.31 ± 18.06 | 0.91 | 403.00 ± 10.94 | 0.75 |

*Paired t-test

After treatment with Donepezil IR 10 mg, there was a significant prolongation of baseline REM sleep time (mean±SE) from 79.75±10.46 min to 119.94±13.53 min (P=0.01), increase in % REM sleep from 19±2 to 30±3 (P=0.01) and reduction in stage 2 sleep time from 162.44±16.87 to 129.44±16.83 (P=0.04)

Thus it can be concluded that treatment with Donepezil formulation of present invention does not prolong REM sleep time and % REM sleep whereas Donepezil IR significantly prolongs REM sleep time and % REM sleep. Thus, despite night-time administration of Donepezil formulation of present invention, REM sleep disturbances with its associated clinical problems can be avoided as compared to Donepezil IR administered at night-time.

The foregoing examples are illustrative embodiments and are merely exemplary. A person skilled in the art may make variations and modifications without deviating from the spirit and scope of the invention. All such modifications and variations are intended to be included within the scope of the claims.

Example 1

| Ingredients | Quantity in % (w/w) |
|---|---|
| Active Layer | |
| Donepezil HCl | 2.0 |
| Hydroxy propyl methyl cellulose | 19.4 |
| Lactose | 20.1 |
| Sodium Starch Glycolate | 3.3 |
| Hydroxy Propyl Cellulose | 2.0 |
| Microcrystalline Cellulose | 5.3 |
| Colloidal Silicon Dioxide | 0.7 |
| Magnesium Stearate | 0.7 |
| Purified Water | qs |
| Inert Swellable Layer | |
| Hydroxy propyl methyl cellulose | 12.0 |
| Polyethylene Oxide | 12.0 |

-continued

| Ingredients | Quantity in % (w/w) |
|---|---|
| Lactose | 14.5 |
| Colloidal Silicon Dioxide | 0.7 |
| Magnesium Stearate | 0.7 |

-continued

| Ingredients | Quantity in % (w/w) |
|---|---|
| Coating | |
| Ethyl Cellulose | 3.7 |
| Hydroxy propyl methyl cellulose | 1.6 |
| Triethyl Citrate | 1.3 |
| Isopropyl Alcohol | qs |
| Dichloromethane | qs |
| Total Coated Tablet Weight | 100.0 |

Brief Manufacturing Procedure:

1. Active Layer
    1.1 Donepezil HCl, sodium starch glycolate, hydroxylpropylmethylcellulose, lactose and hydroxypropylcellulose are weighed, sifted and mixed together.
    1.2 The mixture of step 1.1 is granulated using purified water with suitable granulation parameters and the granules are then dried.
    1.3 The dried granules are sifted through a suitable sieve.
    1.4 The remaining quantities of hydroxylpropylmethylcellulose, lactose and microcrystalline cellulose are sifted through a suitable sieve and mixed with the granules of step 1.3.
    1.5 Colloidal silicon dioxide and magnesium stearate are sifted through a suitable sieve and mixed with the blend of step 1.4.
2. Inert Swellable Layer
    2.1 Hydroxypropylmethylcellulose, polyethylene oxide, lactose and colloidal silicon dioxide are weighed and sifted together.
    2.2 The blend of step 2.1 is lubricated with magnesium stearate which is sifted through a suitable sieve.
3. The blend of steps 1.5 and 2.2 is compressed into a bilayer tablet using oval shape punch using suitable physical parameters.
4. Ethyl cellulose, hydroxypropylmethylcellulose and triethyl citrate are dissolved in a mixture of isopropyl alcohol and dichloromethane with continuous stirring.
5. The compressed tablets of step 3 are coated using coating solution of step 4 with suitable coating parameters.
6. Dissolution study was carried out using USP-II, paddle apparatus at 50 rpm in 0.1N HCl and 6.8 pH phosphate buffer (P.B). (Table 4)

TABLE 4

Dissolution data of donepezil composition prepared by Example 1

| Time (hr) | Dissolution in 0.1N HCl | Dissolution in 6.8 pH P.B |
|---|---|---|
| 0 | 0 | 0 |
| 3 | 0 | 1 |
| 4 | 0 | 1 |
| 5 | 0 | 1 |
| 6 | 1 | 2 |
| 8 | 19 | 38 |
| 10 | 48 | 67 |
| 12 | 70 | 82 |
| 14 | 84 | 88 |

Example 2

| Ingredients | Quantity in % w/w |
|---|---|
| Donepezil HCl | 1.89 |
| Hydroxy Propyl Methyl Cellulose | 25.30 |
| Lactose | 40.95 |
| Sodium Starch Glycolate | 6.96 |
| Hydroxy Propyl Cellulose | 3.79 |
| Microcrystalline Cellulose | 11.77 |
| Colloidal Silicon Dioxide | 0.88 |
| Magnesium Stearate | 0.88 |
| Purified water | qs |
| Coating | |
| Ethyl Cellulose | 4.43 |
| Hydroxy Propyl Methyl Cellulose | 1.89 |
| Triethyl Citrate | 1.26 |
| Isopropyl Alcohol | qs |
| Dichloromethane | qs |
| Total Coated Tablet Weight | 100 |

Brief Manufacturing Procedure:

1. Donepezil HCl, sodium starch glycolate, hydroxypropylmethylcellulose, lactose and hydroxy propyl cellulose are weighed, sifted and mixed together.
2. The mixture of step 1 is granulated using purified water with suitable granulation parameters and the granules are then dried.
3. The dried granules are sifted through a suitable sieve.
4. The remaining quantities of hydroxylpropylmethylcellulose, lactose and microcrystalline cellulose are sifted through a suitable sieve and mixed with the granules of step 3.
5. Colloidal silicon dioxide and magnesium stearate are sifted through a suitable sieve and mixed with the blend of step 4.
6. The lubricated blend of step 5 is compressed using a round shape punch with suitable physical parameters.
7. Ethyl cellulose, hydroxypropylmethyl cellulose and triethyl citrate are dissolved in a mixture of isopropyl alcohol and dichloromethane with continuous stirring.
8. The compressed tablets of step 6 are coated using coating solution of step 7 with suitable coating parameters.
9. Dissolution study was carried out using USP-II, paddle apparatus at 50 rpm in 0.1N HCl and 6.8 pH phosphate buffer (P.B). (Table 5)

TABLE 5

Dissolution data of donepezil composition prepared by Example 1

| Time (hr) | Dissolution in 0.1N HCl | Dissolution in 6.8 pH P.B |
|---|---|---|
| 0 | 0 | 0 |
| 3 | 0 | 1 |
| 4 | 0 | 1 |
| 5 | 0 | 1 |
| 6 | 1 | 2 |
| 8 | 19 | 38 |
| 10 | 48 | 67 |
| 12 | 70 | 82 |
| 14 | 84 | 88 |

Example 3

| Ingredients | Quantity in % w/w |
| --- | --- |
| Donepezil HCl | 2.00 |
| Hydroxy Propyl Methyl Cellulose | 26.40 |
| Lactose | 39.50 |
| Sodium Starch Glycolate | 7.20 |
| Hydroxy Propyl Cellulose | 3.90 |
| Microcrystalline Cellulose | 11.33 |
| Colloidal Silicon Dioxide | 0.90 |
| Magnesium Stearate | 0.90 |
| Purified water | qs |
| Coating | |
| Eudragit RSPO | 5.30 |
| Eudragit L100-55 | 1.30 |
| Triethyl Citrate | 1.30 |
| Isopropyl Alcohol | qs |
| Acetone | qs |
| Total Coated Tablet Weight | 100 |

Brief Manufacturing Procedure:
1. Donepezil HCl, sodium starch glycolate, hydroxypropylmethylcellulose, lactose and hydroxy propyl cellulose are weighed, sifted and mixed together.
2. The mixture of step 1 is granulated using purified water with suitable granulation parameters and the granules are then dried.
3. The dried granules are sifted through a suitable sieve.
4. The remaining quantities of hydroxylpropylmethylcellulose, lactose and microcrystalline cellulose are sifted through a suitable sieve and mixed with the granules of step 3.
5. Colloidal silicon dioxide and magnesium stearate are sifted through a suitable sieve and mixed with the blend of step 4.
6. The lubricated blend of step 5 is compressed using a round shape punch with suitable physical parameters.
7. Eudragit RSPO, Eudragit L100-55, hydroxypropylmethyl cellulose and triethyl citrate are dissolved in a mixture of isopropyl alcohol and acetone with continuous stirring.
8. The compressed tablets of step 6 are coated using coating solution of step 7 with suitable coating parameters.

Example 4

| Ingredients | Quantity in % w/w |
| --- | --- |
| Hardened Sugar Spheres | 50.00 |
| Donepezil HCl | 8.33 |
| Hydroxy Propyl Methyl Cellulose | 4.50 |
| Hydroxy Propyl Cellulose | 8.00 |
| Talc | 1.94 |
| Triethyl Citrate | 0.28 |
| Isopropyl Alcohol | qs |
| Methylene Chloride | qs |
| Purified water | qs |
| Coating | |
| Eudragit RLPO | 2.78 |
| Eudragit RSPO | 19.44 |
| Dibutyl Sebacate | 4.72 |
| Isopropyl Alcohol | qs |
| Acetone | qs |
| Total Weight of Pellets | 100.00 |
| Empty Hard Gelatin Capsules | |

Brief Manufacturing Procedure:
1. Sugar Spheres Hardening
   1.1 The sugar spheres are sifted using vibratory sifter.
   1.2 Triethyl citrate and hydroxypropylmethylcellulose are dissolved in a mixture of Isopropyl alcohol and methylene chloride under continuous stirring.
   1.3 The sugar spheres are loaded in the fluidized bed processor and the fluidization is started.
   1.4 The entire solution of step 1.2 is sprayed onto the sugar spheres at a suitable temperature.
   1.5 The hardened sugar spheres of step 1.4 are dried in the fluidized bed processor at suitable temperature.
   1.6 The dried hardened sugar spheres of step 1.5 are sifted through suitable sieves and the fines are discarded.
2. Drug Loading
   2.1 Hydroxy propyl cellulose is added to purified water to obtain a clear solution.
   2.2 Donepezil hydrochloride is added to the solution of step 2.1 to obtain a clear solution.
   2.3 Talc is added to the solution of step 2.2 under continuous stirring and the dispersion is filtered through a suitable sieve.
   2.4 The dried hardened sugar spheres of step 1.6 are loaded in the fluidized bed processor and the fluidization is started.
   2.5 The entire dispersion of step 2.3 is sprayed onto the hardened sugar spheres at a suitable temperature.
   2.6 The drug loaded pellets of step 2.5 are sifted through suitable sieves and the agglomerates and fines are discarded.
3. Coating step
   3.1 Eudragit and dibutylsebacate are dissolved in a mixture of Isopropyl alcohol and Acetone with continuous stirring.
   3.2 The drug-loaded pellets of step 2.6 are coated using the solution of step 3.1 with suitable coating parameters.
   3.3 The coated pellets of step 3.2 are filled in hard gelatin capsule shells with required fill weight.

Example 5

| Ingredients | Quantity in % w/w |
| --- | --- |
| Donepezil HCl | 3.8 |
| Eudragit RLPO | 1.3 |
| Eudragit L100-55 | 18.8 |
| Eudragit RSPO | 8.8 |
| Lactose | 37.1 |
| Hydroxy Propyl Cellulose | 5.0 |
| Microcrystalline Cellulose | 18.3 |
| Colloidal Silicon Dioxide | 1.0 |
| Magnesium Stearate | 0.8 |
| Purified water | qs |
| Coating | |
| Ethyl cellulose | 2.8 |
| Hydroxy propyl methyl cellulose | 1.30 |
| Dibutyl Sebacate | 1.0 |
| Isopropyl Alcohol | qs |
| Dichloromethane | qs |
| Total Coated Tablet Weight | 100 |

Brief Manufacturing Procedure:
1. Donepezil HCl, Eudragit RLPO, Eudragit L100-55, Eudragit RSPO, lactose and hydroxy propyl cellulose are weighed, sifted and mixed together.

2. The mixture of step 1 is granulated using purified water with suitable granulation parameters and the granules are then dried.
3. The dried granules are sifted through a suitable sieve.
4. Microcrystalline cellulose, colloidal silicon dioxide and magnesium stearate are sifted through a suitable sieve and mixed with the blend of step 3.
5. The lubricated blend of step 4 is compressed using a round shape punch with suitable physical parameters.
6. Ethyl cellulose, hydroxypropylmethyl cellulose and dibutylsebacate are dissolved in a mixture of isopropyl alcohol and dichloromethane with continuous stirring.
7. The compressed tablets of step 5 are coated using coating solution of step 6 with suitable coating parameters.

Example 6

| Ingredients | Quantity in % w/w |
|---|---|
| Active Layer | |
| Donepezil HCl | 4.76 |
| Polyvinyl pyrrolidone | 1.59 |
| Mannitol | 15.90 |
| Polyethylene Oxide | 14.29 |
| Magnesium stearate | 0.95 |
| Isopropyl Alcohol | qs |
| Push-pull Layer | |
| Polyethylene oxide | 7.94 |
| Potassium Chloride | 15.88 |
| Hydroxy propyl methyl cellulose | 14.29 |
| Polyvinyl pyrrolidone | 3.18 |
| Magnesium Stearate | 0.64 |
| Semi Permeable coating | |
| Cellulose acetate | 7.94 |
| Triethyl Citrate | 1.59 |
| Acetone | qs |
| Functional Coating | |
| Eudragit L100-55 | 7.94 |
| Triethyl Citrate | 3.11 |
| Isopropyl Alcohol | qs |
| Acetone | qs |
| Total Coated Tablet Weight | 100 |

Brief Manufacturing Procedure
1. Donepezil HCl, mannitol and polyethylene oxide are sifted and mixed together.
2. The mixture of step 1 is granulated with polyvinyl pyrrolidone solution in isopropyl alcohol.
3. The granules of step 2 are dried and sifted through a suitable sieve.
4. The dried granules of step 3 are lubricated using magnesium stearate.
5. Polyethylene oxide, potassium chloride and hydroxy propyl methyl cellulose are sifted and mixed together and lubricated using magnesium stearate.
6. The granules of step 4 and mixture of step 5 are compressed as bilayered tablets using a round shape punch with suitable physical parameters.
7. Cellulose acetate and triethyl citrate are dissolved in acetone with stirring.
8. The compressed tablets of step 6 are coated using coating solution of step 7 with suitable coating parameters.
9. The coated tablets of step 8 are drilled with laser drilling technology on one or both sides.
10. Eudragit L100-55 and triethyl citrate are dissolved in a mixture of isopropyl alcohol and acetone with continuous stirring.
11. The coated tablets of step 9 are coated using coating solution of step 10 with suitable coating parameters.

The invention claimed is:

1. A timed release pharmaceutical composition administered orally at night, comprising donepezil in an amount selected from 3 mg to 50 mg, wherein the composition is a coated composition, which comprises: a) a core comprising donepezil and one or more release controlling agent(s), and b) a functional coating comprising one or more release controlling agent(s) in an amount of about 1% to about 40% by total weight of the composition, wherein the composition exhibits the following in vitro dissolution profile when tested in a Paddle dissolution apparatus at 50 rpm in 900 ml 6.8 buffer at 37° C.

less than about 20% w/w of donepezil is released in 6 hrs, and more than 90% w/w of donepezil is released after 12 hrs.

2. The timed release pharmaceutical composition according to claim 1, when administered orally provides reduced incidence of insomnia and nightmares.

3. The timed release pharmaceutical composition according to claim 1, when administered orally provides reduced incidence of sundowning syndrome.

4. The timed release pharmaceutical composition according to claim 1, wherein the said composition shortens the titration period required for donepezil administration.

5. The timed release pharmaceutical composition according to claim 4, wherein the said composition shortens the titration period required for donepezil administration by two to four weeks.

6. The timed release pharmaceutical composition according to claim 1, wherein the said composition is used to treat a patient suffering from a disease or a condition characterized by symptoms of dementia and/or cognitive impairments.

7. The timed release pharmaceutical composition according to claim 1, wherein the said composition is used to treat a patient suffering from mild, moderate or severe Alzheimer's disease.

8. A timed release pharmaceutical composition comprising donepezil in an amount selected from 3 mg to 50 mg, wherein the composition is a coated composition, which comprises: a) a core comprising donepezil and one or more release controlling agent(s), and b) a functional coating comprising one or more release controlling agent(s) in an amount of about 1% to about 40% by total weight of the composition, wherein the single dose $AUC_{(2-10)}$ of the said composition is about 55% to about 95% less than the single dose $AUC_{(2-10)}$ of an immediate release composition of donepezil, wherein both the compositions have the same dose of donepezil and are administered orally at night.

9. The timed release pharmaceutical composition according to claim 8, wherein the said composition provides reduced incidence of insomnia and nightmares.

10. The timed release pharmaceutical composition according to claim 8, wherein the said composition shortens the titration period required for donepezil administration.

11. The timed release pharmaceutical composition according to claim 8, wherein the said composition shortens the titration period required for donepezil administration by two to four weeks.

12. The timed release pharmaceutical composition according to claim 8, wherein the said composition is used to treat a patient suffering from a disease or a condition characterized by symptoms of dementia and/or cognitive impairments.

13. The timed release pharmaceutical composition according to claim 8, wherein the said composition is used to treat a patient suffering from mild, moderate or severe Alzheimer's disease.

14. A timed release pharmaceutical composition comprising donepezil in an amount selected from 3 mg to 50 mg, wherein the composition is a coated composition, which comprises: a) a core comprising donepezil and one or more release controlling agent(s) in an amount of about 1% to about 40% by total weight of the composition, and b) a functional coating comprising one or more release controlling agent(s) wherein the steady state AUC (2-10) of the said composition is about 10% to about 20% less than the steady state AUC (2-10) of an immediate release composition of donepezil, wherein both the compositions have the same dose of donepezil and are administered orally at night.

15. The timed release pharmaceutical composition according to claim 14, wherein the said composition provides reduced incidence of insomnia and nightmares.

16. The timed release pharmaceutical composition according to claim 14, wherein the said composition shortens the titration period required for donepezil administration.

17. The timed release pharmaceutical composition according to claim 14, wherein the said composition shortens the titration period required for donepezil administration by two to four weeks.

18. The timed release pharmaceutical composition according to claim 14, wherein the said composition is used to treat a patient suffering from a disease or a condition characterized by symptoms of dementia and/or cognitive impairments.

19. The timed release pharmaceutical composition according to claim 14, wherein the said composition is used to treat a patient suffering from mild, moderate or severe Alzheimer's disease.

20. A timed release pharmaceutical composition comprising donepezil in an amount selected from 3 mg to 50 mg, wherein the composition is a coated composition, which comprises: a) a core comprising donepezil and one or more release controlling agent(s), and b) a functional coating comprising one or more release controlling agent(s) in an amount of about 1% to about 40% by total weight of the composition, wherein the single dose $AUC_{(19-22)}$ of the said composition is about 10% to about 50% more than the single dose $AUC_{(19-22)}$ of an immediate release composition of donepezil, wherein both the compositions have the same dose of donepezil and are administered orally at night.

21. The timed release pharmaceutical composition according to claim 20, wherein the said composition provides reduced incidence of sundowning syndrome.

22. The timed release pharmaceutical composition according to claim 20, wherein the said composition is used to treat a patient suffering from a disease or a condition characterized by symptoms of dementia and/or cognitive impairments.

23. The timed release pharmaceutical composition according to claim 20, wherein the said composition is used to treat a patient suffering from mild, moderate or severe Alzheimer's disease.

24. A timed release pharmaceutical composition comprising donepezil in an amount selected from 3 mg to 50 mg, wherein the composition is a coated composition, which comprises: a) a core comprising donepezil and one or more release controlling agent(s), and b) a functional coating comprising one or more release controlling agent(s) in an amount of about 1% to about 40% by total weight of the composition, wherein the steady state $AUC_{(19-22)}$ of the said composition is about 10% to about 100% more than the steady state $AUC_{(19-22)}$ of an immediate release composition of donepezil, wherein both the compositions have the same dose of donepezil and are administered orally at night.

25. The timed release pharmaceutical composition according to claim 24, wherein the said composition provides reduced incidence of sundowning syndrome.

26. The timed release pharmaceutical composition according to claim 24, wherein the said composition is used to treat a patient suffering from a disease or a condition characterized by symptoms of dementia and/or cognitive impairments.

27. The timed release pharmaceutical composition according to claim 24, wherein the said composition is used to treat a patient suffering from mild, moderate or severe Alzheimer's disease.

* * * * *